United States Patent
Korn

(10) Patent No.: US 10,854,338 B2
(45) Date of Patent: Dec. 1, 2020

(54) PREDICTING BREAST CANCER RESPONSIVENESS TO HORMONE TREATMENT USING QUANTITATIVE TEXTURAL ANALYSIS

(71) Applicant: Imaging Endpoints II LLC, Scottsdale, AZ (US)

(72) Inventor: Ronald L. Korn, Paradise Valley, AZ (US)

(73) Assignee: IMAGING ENDPOINTS II LLC, Scottsdale, AZ (US)

( * ) Notice: Subject to any disclaimer, the term of this patent is extended or adjusted under 35 U.S.C. 154(b) by 368 days.

(21) Appl. No.: 15/472,466

(22) Filed: Mar. 29, 2017

(65) Prior Publication Data

US 2018/0285531 A1    Oct. 4, 2018

(51) Int. Cl.
*G16H 50/30* (2018.01)
*G16H 50/50* (2018.01)

(52) U.S. Cl.
CPC ............ *G16H 50/50* (2018.01); *G16H 50/30* (2018.01); *C12Q 2600/16* (2013.01); *G01N 2800/50* (2013.01)

(58) Field of Classification Search
CPC .... G01N 2800/50; G16H 50/30; G16H 50/50; C21Q 1/6886; C21Q 2600/106

USPC ............... 703/2; 382/132; 506/12; 435/6.14; 536/24.22

See application file for complete search history.

(56) References Cited

U.S. PATENT DOCUMENTS

| | | | | |
|---|---|---|---|---|
| 7,306,921 | B2* | 12/2007 | Nevalainen | G01N 33/5011 435/7.1 |
| 10,001,484 | B2* | 6/2018 | Egland | G01N 33/564 |
| 2009/0104596 | A1* | 4/2009 | Assadi-Porter | C12Q 1/6883 435/5 |
| 2009/0232910 | A1* | 9/2009 | Schmechel | A61K 38/57 424/722 |
| 2015/0094224 | A1* | 4/2015 | Walfish | C12Q 1/6886 506/9 |
| 2015/0126392 | A1* | 5/2015 | Yi | C12Q 1/6886 506/9 |
| 2015/0268241 | A1* | 9/2015 | Egland | G01N 33/564 514/789 |
| 2017/0107577 | A1* | 4/2017 | Al-Ejeh | C12Q 1/6886 |

* cited by examiner

*Primary Examiner* — Thai Q Phan
(74) *Attorney, Agent, or Firm* — Quarles & Brady LLP

(57) ABSTRACT

Biomarker signatures for predicting breast cancer tumor aggressiveness. The signatures are derived from QTA-based parameters from a first population of low risk scores and a second population of high risk scores. The signatures may be expressed in the form log (RS)=Mx+B for linear modeling, or for logistic modeling the signatures may be expressed as either p=ex/[1+ex] where x=Ay+B, or in the form log it(p)=C(PR)+Ay+B, where y is a QTA based parameter.

21 Claims, 17 Drawing Sheets

| Primary QTA Parameters | Primary QTA Parameters Normalized to Total Numbers of Pixels (Derived) | Range of Primary Parameters Across SSF Levels (Derived) | Difference Between Primary QTA Parameters Between Tumor and Normal Tissues (Derived) |
|---|---|---|---|
| Mean | Mean / Total | Mean $_{high}$ - Mean $_{low}$ | Mean $_{tumor}$ - Mean $_{normal}$ |
| SD | SD / Total | SD $_{high}$ - SD $_{low}$ | SD $_{tumor}$ - SD $_{normal}$ |
| Entropy | Entropy / Total | Entropy $_{high}$ - Entropy $_{low}$ | Entropy $_{tumor}$ - Entropy $_{normal}$ |
| MPP | MPP / Total | MPP $_{high}$ - MPP $_{low}$ | MPP $_{tumor}$ - MPP $_{normal}$ |
| Skewness | Skewness / Total | Skewness $_{high}$ - Skewness $_{low}$ | Skewness $_{tumor}$ - Skewness $_{normal}$ |
| Kurtosis | Kurtosis / Total | Kurtosis $_{high}$ - Kurtosis $_{low}$ | Kurtosis $_{tumor}$ - Kurtosis $_{normal}$ |
| 302 | 304 | 306 | 308 |

| Primary QTA Parameters | Primary QTA Parameters Normalized to Total Numbers of Pixels (Derived) | Range of Primary Parameters Across SSF Levels (Derived) | Difference Between Primary QTA Parameters Between Tumor and Normal Tissues (Derived) |
|---|---|---|---|
| Mean | Mean / Total | $Mean_{high} - Mean_{low}$ | $Mean_{tumor} - Mean_{normal}$ |
| SD | SD / Total | $SD_{high} - SD_{low}$ | $SD_{tumor} - SD_{normal}$ |
| Entropy | Entropy / Total | $Entropy_{high} - Entropy_{low}$ | $Entropy_{tumor} - Entropy_{normal}$ |
| MPP | MPP / Total | $MPP_{high} - MPP_{low}$ | $MPP_{tumor} - MPP_{normal}$ |
| Skewness | Skewness / Total | $Skewness_{high} - Skewness_{low}$ | $Skewness_{tumor} - Skewness_{normal}$ |
| Kurtosis | Kurtosis / Total | $Kurtosis_{high} - Kurtosis_{low}$ | $Kurtosis_{tumor} - Kurtosis_{normal}$ |

| QTA parameter | Transformed QTA parameter |
|---|---|
| Mean | *log*(Mean + 400) |
| Kurtosis | *log*(Kurtosis + 2) |
| Mean-Total | *Sqrt*(Mean-Total) |
| SD-Total | *log*(SD-Total) |
| Entropy-Total | *log*(Entropy-Total) |
| MPP-Total | *log*(MPP-Total) |
| Kurtosis-Total | *Sqrt*(Kurtosis-Total) |
| SD-Range | *Sqrt*(SD-Range) |
| Skewness-Range | *log*(Skewness-Range) |
| Kurtosis-Range | *log*(Kurtosis-Range) |

| ER | PR | | |
|---|---|---|---|
|  | Positive | Negative | Total |
| Positive | 56 | 7 | 63 |
| Negative | 1 | 0 | 1 |
| Total | 57 | 7 | 64 |

FIG. 5

|  | PR | | Total |
| --- | --- | --- | --- |
| RS Risk Group | Positive | Negative | |
| Low Risk (RS < 18) | 35 | 0 | 35 |
| Intermediate Risk (18 <= RS < 30) | 19 | 3 | 22 |
| High Risk (RS > 30) | 3 | 4 | 7 |
| Total | 57 | 7 | 64 |

FIG. 6

|  | PR | | Total |
| --- | --- | --- | --- |
| RS Risk Group | Positive | Negative | |
| Low Risk (RS < 11) | 9 | 0 | 9 |
| Intermediate Risk (11 <= RS <= 25) | 42 | 1 | 43 |
| High Risk (RS > 25) | 6 | 6 | 12 |
| Total | 57 | 7 | 64 |

FIG. 7

| SSF | QTA Parameter | Sample Size (n) | Mean | Standard Deviation | Minimum | Maximum |
|---|---|---|---|---|---|---|
| 0.4 | Mean | 65 | 68.60708 | 55.85314 | -12.01 | 316.61 |
| 0.4 | SD | 65 | 634.9731 | 154.9119 | 348.56 | 1031.47 |
| 0.4 | Entropy | 65 | 7.653379 | 0.2358882 | 7.17405 | 8.04565 |
| 0.4 | MPP | 65 | 517.3695 | 131.9921 | 272.202 | 838.151 |
| 0.4 | Skewness | 65 | -0.09662 | 0.3005977 | -1.7556 | 0.4905 |
| 0.4 | Kurtosis | 65 | 0.5355985 | 1.097498 | -0.5714 | 7.7133 |
| 0.6 | Mean | 65 | 149.7208 | 109.6911 | -16.94 | 570.49 |
| 0.6 | SD | 65 | 765.0869 | 211.1919 | 404.45 | 1497.25 |
| 0.6 | Entropy | 65 | 7.796314 | 0.2568659 | 7.25682 | 8.26074 |
| 0.6 | MPP | 65 | 654.8278 | 192.9854 | 335.024 | 1274.12 |
| 0.6 | Skewness | 65 | -0.1088385 | 0.335995 | -1.5016 | 0.7663 |
| 0.6 | Kurtosis | 65 | 0.4318538 | 0.9044054 | -0.5396 | 4.7585 |
| 0.8 | Mean | 65 | 256.7908 | 169.9689 | -14.52 | 785.95 |
| 0.8 | SD | 65 | 865.8097 | 261.5368 | 461.5 | 1750.13 |
| 0.8 | Entropy | 65 | 7.885341 | 0.2633471 | 7.30915 | 8.43365 |
| 0.8 | MPP | 65 | 787.6868 | 258.1746 | 403.857 | 1750.13 |

| SSF | QTA Parameter | Sample Size (n) | Mean | Standard Deviation | Minimum | Maximum |
|---|---|---|---|---|---|---|
| 0.8 | Skewness | 65 | -0.1185754 | 0.393803 | -1.1378 | 0.9672 |
| 0.8 | Kurtosis | 65 | 0.3651415 | 0.987174 | -0.8932 | 4.2965 |
| 1 | Mean | 65 | 385.6463 | 235.56 | 2.22 | 1003.88 |
| 1 | SD | 65 | 944.4589 | 307.0153 | 492.44 | 2137.81 |
| 1 | Entropy | 65 | 7.945265 | 0.2764926 | 7.32828 | 8.5702 |
| 1 | MPP | 65 | 920.5114 | 323.4779 | 430.198 | 2141.74 |
| 1 | Skewness | 65 | -0.1165585 | 0.4346557 | -1.4324 | 0.9026 |
| 1 | Kurtosis | 65 | 0.2624369 | 1.140967 | -0.9769 | 5.7072 |
| 0 | Mean | 65 | 2534.86 | 429.3455 | 1385.75 | 3387.36 |
| 0 | SD | 65 | 444.3408 | 150.9218 | 243.61 | 938.4 |
| 0 | Entropy | 65 | 6.571937 | 0.3008233 | 6.07411 | 7.33031 |
| 0 | MPP | 65 | 2534.86 | 429.3455 | 1385.75 | 3387.36 |
| 0 | Skewness | 65 | -0.4918954 | 0.4406189 | -1.7215 | 0.3882 |
| 0 | Kurtosis | 65 | 0.22204 | 0.858151 | -1.1182 | 3.2106 |

FIG. 8B

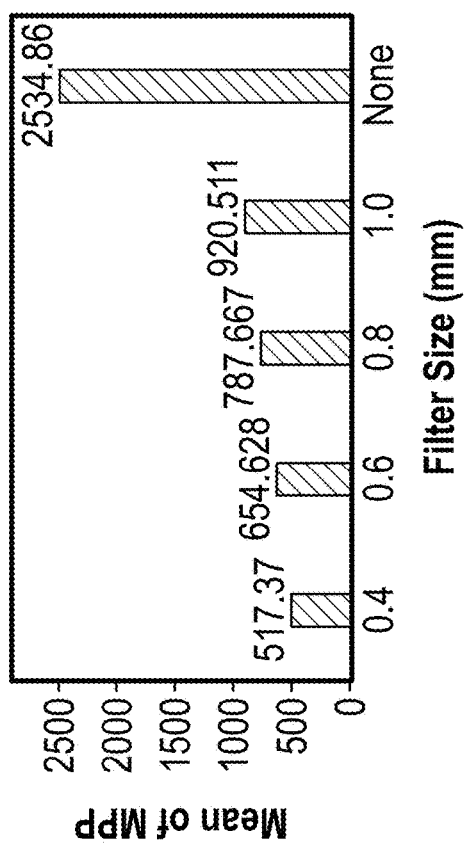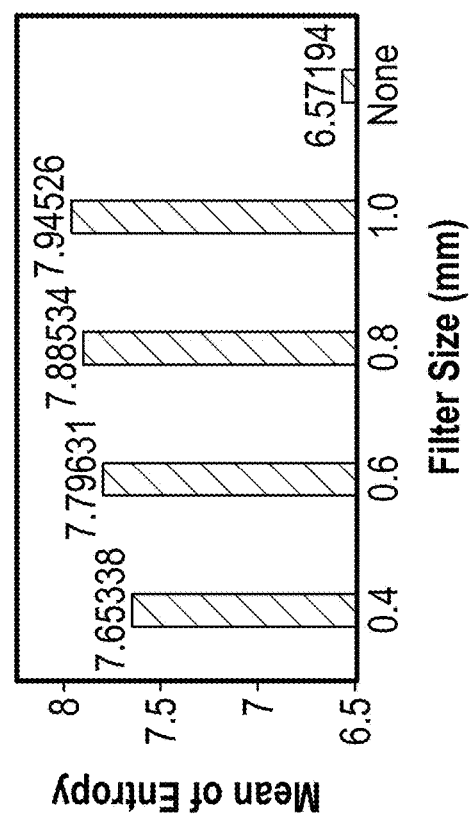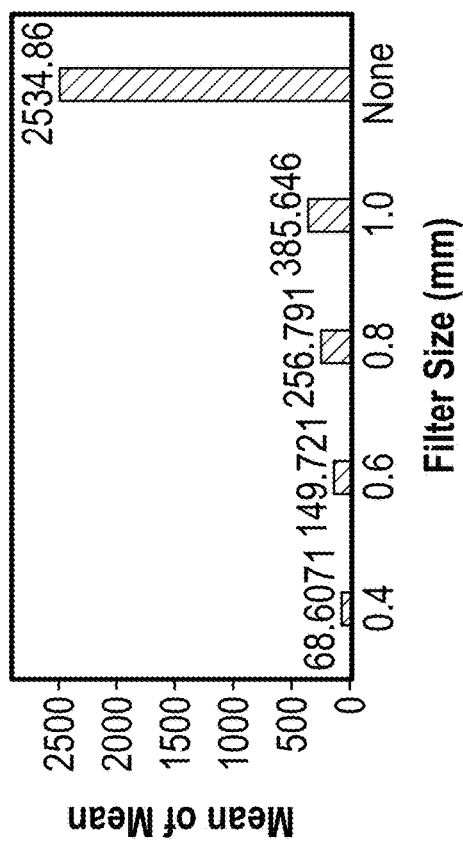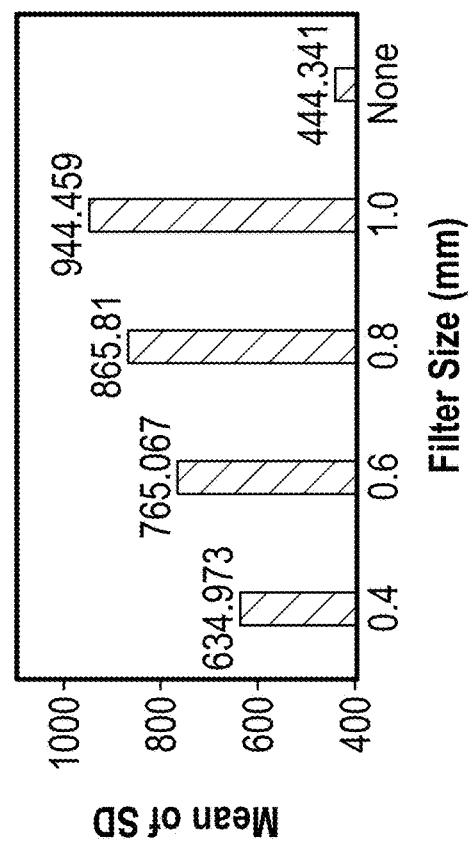
FIG. 9A

| ssf | Risk Group | n | Mean | SE | SD | t | p-value | Diff | Diff SE |
|---|---|---|---|---|---|---|---|---|---|
| 0.4 | High | 7 | 26.35 | 7.809821 | 20.66284 | - | - | - | - |
| 0.4 | Mid vs. High | 22 | 62.8909 | 8.97 | 42.07303 | 3.0724 | 0.0057 | 36.54091 | 11.89345 |
| 0.4 | Low vs. High | 36 | 80.3169 | 10.6071 | 63.64258 | 4.0971 | 0.0003 | 53.96694 | 13.17208 |
| 0.4 | Low vs. Mid | - | - | - | - | 1.2544 | 0.2149 | 17.42604 | 13.89141 |
| 0.6 | High | 7 | 63.52 | 16.08923 | 42.56809 | - | - | - | - |
| 0.6 | Mid vs. High | 22 | 140.6391 | 18.55678 | 87.03902 | 3.1400 | 0.0048 | 77.11909 | 24.56048 |
| 0.6 | Low vs. High | 36 | 172.0319 | 20.47731 | 122.8638 | 4.1668 | 0.0003 | 108.5119 | 26.04195 |
| 0.6 | Low vs. Mid | - | - | - | - | 1.1360 | 0.2609 | 31.39285 | 27.63466 |
| 0.8 | High | 7 | 119.5986 | 25.72049 | 68.05003 | - | - | - | - |
| 0.8 | Mid vs. High | 22 | 245.3786 | 30.12085 | 141.2793 | 3.1756 | 0.0044 | 125.7801 | 39.60819 |

FIG. 10A

| ssf | Risk Group | n | Mean | SE | SD | t | p-value | Diff | Diff SE |
|---|---|---|---|---|---|---|---|---|---|
| 0.8 | Low vs. High | 36 | 290.4411 | 31.20084 | 187.2051 | 4.2251 | 0.0002 | 170.8425 | 40.43558 |
| 0.8 | Low vs. Mid | - | - | - | - | 1.0391 | 0.3035 | 45.06247 | 43.36771 |
| 1 | High | 7 | 193.9643 | 36.86359 | 97.53188 | - | - | - | - |
| 1 | Mid vs. High | 22 | 372.5791 | 42.63327 | 199.9677 | 3.1691 | 0.0045 | 178.6148 | 56.36062 |
| 1 | Low vs. High | 36 | 430.9033 | 42.90795 | 257.4477 | 41.1885 | 0.0003 | 236.939 | 56.56869 |
| 1 | Low vs. Mid | - | - | - | - | 0.9642 | 0.3393 | 58.32424 | 60.48709 |
| 0 | High | 7 | 2661.97 | 130.1412 | 344.3212 | - | - | - | - |
| 0 | Mid vs. High | 22 | 2516.122 | 92.67463 | 434.6826 | -0.9129 | 0.3783 | -145.8477 | 159.7664 |
| 0 | Low vs. High | 36 | 2521.595 | 74.48862 | 446.9317 | -0.9361 | 0.3705 | -140.375 | 149.9509 |
| 0 | Low vs. Mid | - | - | - | - | 0.0460 | 0.9635 | 5.472727 | 118.8997 |

FIG. 10B

| PR Status | SSF | Out-come | Predictors | Linear Models | n | F | p | R² | Condition Number |
|---|---|---|---|---|---|---|---|---|---|
| Not Included | 0.4 | log(RS) | SD | log(RS)= -0.0004177*(SD) +1.500248 | 65 | 6.89 | 0.0108 | 0.0870 | 17.8116 |
| Included | 1 | log(RS) | PR, Skewness-Diff | log(RS)= -0.3759396*(PR) +0.07859932* (Skewness-Diff) +1.592273 | 65 | 15.30 | < 0.0001 | 0.2988 | 12.3685 |
| PR+ Only | 0.8 | log(RS) | Skewness-Diff | log(RS)= 0.3033226* (Skewness-Diff) +2.83791 | 58 | 9.36 | 0.0034 | 0.1320 | 14.7062 |

| PR Status | Pr | Predictors | Logistic Models | SSF | n | chi² | p | AUC | SE |
|---|---|---|---|---|---|---|---|---|---|
| Not Included | RS>30 | Entropy-Diff | p=exp(x)/[1+exp(x)] where x=-5.905371*(Entropy-Diff)-2.254296 | 0 | 65 | 10.98 | 0.0009 | 0.8424 | 0.0717 |
| Not Included | RS>25 | Mean-Total | p=exp(x)/[1+exp(x)] where x=-140.8101*(Mean-Total)-0.2993403 | 0.6 | 65 | 9.98 | 0.0016 | 0.7437 | 0.0612 |
| Included | RS>30 | PR, SD-Diff | logit (p)=-3.548941*(PR)-0.0092257*(SD-Diff) + 0.363196 | 0 | 65 | 18.69 | 0.0001 | 0.9409 | 0.0322 |
| Included | RS>25 | PR, Mean-Total | logit (p)=-4.321735*(PR)-159.0879*(Mean-Total) + 3.430188 | 0.6 | 65 | 25.56 | <0.0001 | 0.8443 | 0.0591 |
| PR+ Only | RS>30 | SD-Diff | p=exp(x)/[1+exp(x)] where x=-0.0124166*(SD-Diff)-3.547383 | 0 | 58 | 6.87 | 0.0087 | 0.9212 | 0.0515 |
| PR+ Only | RS>25 | MPP-Diff Skewness-Diff | logit (p)=-0.0095748*(MPP-Diff) + 6.487719*(Skewness-Diff) - 2.761748 | 0.6 | 58 | 16.17 | 0.0003 | 0.9103 | 0.0482 |

PREDICTING BREAST CANCER RESPONSIVENESS TO HORMONE TREATMENT USING QUANTITATIVE TEXTURAL ANALYSIS

TECHNICAL FIELD

The present invention relates, generally, to biomarker signatures for assessing breast cancer aggressiveness and, more particularly, to systems and methods for deriving the signatures from imaging data using quantitative textural analysis.

BACKGROUND

Imaging analysis provides a non-invasive, low risk approach to assessing tumor biology prior to administering treatment therapies and an objective pathway for monitoring tumor responsiveness to treatment. An evolving strategy for the non-invasive interrogation of tumors involves analyzing diagnostic images to identify patterns of appearances linked to tumor biology.

Using signals derived from imaging to characterize tumor biology is based on several factors including: (1) tumor images express underlying tumor biology; (2) growth kinetics and other drivers of oncologic transformation may have unique expression patterns on imaging; (3) unique expression patterns can manifest as imaging phenotypes; and (4) the imaging phenotypes can be characterized both qualitatively and quantitatively. Thus, an understanding of disease biology can be derived, measured, inferred or predicted by examining the imaging phenotype or appearance of a tumor by different radiologic means. This coupled with imaging's ability to provide a comprehensive and real-time assessment of the entire tumor and its micro-environment make quantitative imaging an attractive tool for rapid assessment and prognosis.

Qualitative descriptions of the appearance of tumors on imaging can provide some degree of biologic characterization but are open to interpretation and lack standardization and reproducibility. Moreover, although there is general agreement on many qualitative descriptors, reader variability can be broad. Thus, being able to take qualitative features and perform quantitative analysis on imaging is appealing.

The University College in London (UCL) has developed a software platform known as TexRAD that provides quantitative measurements (referred to herein as Quantitative Textural Analysis or QTA) of tumor lesions present on images. QTA is a post-processing technique that can be used to quantify tissue complexity by assessing the distribution of textural features (or heterogeneity) within a tumor lesion and their change following treatment. Studies have shown that tumor complexity is seen in multiple imaging modalities and can be derived from many different image types, sequences or imaging series (e.g. CT, MRI, PET, and Mammography).

Tumor complexity can be quantified by QTA using a range of measurable parameters based on enhancement characteristics and/or density changes on a local level by clustering small groups of pixels together using filter kernels (referred to as spatial scale filters (SSF)) within a lesion itself. The output from the analysis then provides a measure of tumor heterogeneity. However, much of the heterogeneity visible on a radiological image can represent photon noise, which tends to mask or suppress the signal strength of underlying biologic information. By first filtering out the noise, QTA analysis can then be used to more effectively probe the biological diversity inherent in tumor complexity.

In the United States, breast cancer is the second most common cancer among American women, behind skin cancer. Breast cancer is also the second leading cause of cancer death of American women, exceeded only by lung cancer. Approximately one in eight American women will develop invasive breast cancer in their lifetime.

Despite the increasing incidence of breast cancer, mortality due to breast cancer has been steadily declining in major developed countries. However, there still remains much work to be done to understand and treat breast cancer. Currently there is no gold standard therapy to treat all breast cancer tumors. This complexity in treatment is due in part to differential selective pressure generated by the microenvironment and therapeutic interventions, which create various evolutionary pathways and result in the observed heterogeneity in cancer tumors. Tumor heterogeneity is demonstrated by differences in genomic, proteonomic, and metabolic expressions of the tumor cells, as well as differences in the interaction between the tumor cells and the surrounding environment.

The recognition of heterogeneity in cancer tumors has led to targeted therapies which utilize specific predictive and prognostic molecular signals to guide personalized therapy to treat cancer. Many current cancer research efforts are also focused on understanding molecular signals in tumors, for better cancer diagnosis, prognosis, therapy selection, and measurement of treatment response.

The paradigm breast cancer biomarkers are estrogen receptors (ER) and progesterone receptors (PR), which are nuclear hormone receptors. Breast cancer tumors that tested positive for ER and/or PR expression receive remarkable benefits from endocrine therapy such as tamoxifen and aromatase inhibitors (AI), regardless of the age of the patient; whereas breast cancer tumors that are negative for ER and/or PR receive little or no benefits from the same therapy. Another important breast cancer biomarker is HER2 (human epidermal growth factor receptor 2). HER2 protein overexpression or gene amplification is referred to as HER2+. HER2+ breast cancer can benefit from trastuzumab or lapatinib therapy.

Recent studies show that breast cancer can be typed based on its tumor source in the terminal duct: Luminal and Basilar. Tumors derived from the lumen tend to be ER+ and/or PR+, have a prevalence of 60% of all breast cancer, and tend to respond to hormonal therapy. Basilar breast cancer tends to be HER2+, and is more aggressive than Luminal type. Luminal type is further subdivided into subtypes A and B, where Luminal A is less aggressive and is more responsive to hormonal therapy, whereas Luminal B is more aggressive and may require additional chemotherapy.

The test for invasive carcinoma is the Oncotype DX®, which is a genomic assay that analyzes the gene expression of a panel of 21 genes. The assay yields an Oncotype DX® Assay Recurrence Score (RS) ranging from 0 to 100, that correlates to the likelihood of distant recurrence and likelihood of chemotherapy benefits. This assay is included in American Society of Clinical Oncology (ASCO) and National Comprehensive Cancer Network (NCCN) guidelines.

A major advantage of textural analysis (or QTA) is that it does not require invasive procedures such as biopsy nor even additional radiologic imaging; it is applied on routine radiologic images that are already indicated for cancer treatment and monitoring.

Notwithstanding the potential for QTA as a tool for finding imaging biomarkers, reliable signatures for predicting breast cancer aggressiveness without the need for a biopsy remain elusive.

Various features and characteristics of the subject invention will become apparent from the subsequent detailed description and the appended claims, taken in conjunction with the accompanying drawings and this background section.

BRIEF SUMMARY

The present invention provides various biomarker signatures for predicting tumor aggressiveness in breast cancer patients, and thus the ability to determine whether less invasive treatment (e.g., hormone therapy) or more invasive treatment (e.g., chemotherapy) is warranted. The signature is derived from aggregate breast tumor imaging data in conjunction with quantitative textural analysis (QTA), linear modeling, and logistic modeling techniques. Various embodiments involve: i) unambiguously identifying a first population of known low RS score images and a second population of known high RS score images; ii) processing mammography data for both populations using quantitative textural analysis (QTA); iii) generating, for both populations, respective histograms and related quantitative metrics involving mean pixel density, standard deviation of the histogram curve, mean positive pixel value of the pixels that are in the positive value range, entropy, skewness, and kurtosis; iv) performing logistical regression on the quantitative metrics for both populations to yield a plurality of predictive signatures for various filter values; v) performing QTA on a subsequent breast cancer patient; vi) comparing one or more of the signatures to one or more relevant metrics for the subsequent patient; and vii) determining the probability that the subsequent patient has an RS score exceeding a predetermined threshold based on the comparison(s).

In one embodiment, tumor heterogeneity was assessed using QTA on digital mammograms of 64 patients with invasive ductal carcinoma (IDC). The QTA generated values for six primary metrics: i) mean; ii) standard deviation (SD); iii) mean positive pixel (MPP) value; iv) entropy; v) kurtosis; and vi) skewness. Tumor aggressiveness was assessed using patients' Oncotype DX® Recurrence Score (RS), a proven genomic assay score that correlates with the rate of remote breast cancer recurrence. RS and hormonal receptor status—estrogen receptor (ER) and progesterone receptor (PR)—were collected from pathology reports. Data were analyzed using statistical tools including Spearman rank correlation, linear regression, and logistic regression.

Linear regression analysis showed that the QTA parameter (metric) SD was a good predictor of RS (F=6.89, p=0.0108, R2=0.0870) at SSF=0.4. When PR status was included as a predictor, PR status and QTA parameter Skewness-Diff, achieved linear model of greater fit (F=15.302, p<0.0001, R2=0.2988) at SSF=1. Among PR+ patients, Skewness-Diff was a good linear predictor of RS (F=9.36, p=0.0034, R2=0.1320) at SSF=0.8.

Logistic regression analysis showed that several QTA-derived parameters were good predictors of high risk RS probability, using different cutoffs of RS=30 and RS=25 for high risk RS; these QTA-derived parameters were Entropy-Diff for RS>30 (chi$^2$=10.98, p=0.0009, AUC=0.8424, SE=0.0717) and Mean-Total for RS>25 (chi$^2$=9.98, p=0.0016, AUC=0.7437, SE=0.0612). When PR status was included, logistic models of higher log-likelihood chi$^2$ were found with SD-Diff for RS>30 (chi$^2$=18.69, p=0.0001, AUC=0.9409, SE=0.0322), and with Mean-Total for RS>25 (chi$^2$=25.56, p<0.0001, AUC=0.8443, SE=0.0591). For PR+ patients, good predictors were SD-Diff for RS>30 (chi$^2$=6.87, p=0.0087, AUC=0.9212, SE=0.0515), and MPP-Diff and Skewness-Diff for RS>25 (chi$^2$=16.17, p=0.0003, AUC=0.9103, SE=0.0482).

Quantitative measurement of breast cancer tumor heterogeneity using QTA on digital mammograms may thus be used as predictors of predetermined RS threshold values and can potentially allow a non-invasive and cost-effective way to quickly assess the likelihood of high risk RS, thereby informing treatment options.

It should be noted that the various inventions described herein, while illustrated in the context of the embodiments described herein, are not so limited. Those skilled in the art will appreciate that the inventions described herein may contemplate any number of predictive signatures involving, for example, various combinations of QTA-derived parameters, coefficients, and constants.

Various other embodiments, aspects, and features are described in greater detail below.

BRIEF DESCRIPTION OF THE DRAWING FIGURES

Exemplary embodiments will hereinafter be described in conjunction with the appended drawing figures, wherein like numerals denote like elements, and:

FIG. 3 is an exemplary table of derived QTA parameters in accordance with various embodiments;

FIG. 4 is an exemplary table of transformed QTA parameters in accordance with various embodiments;

FIG. 5 is an exemplary table of patient ER and PR status in accordance with various embodiments;

FIG. 6 is an exemplary table of standard RS risk groups with PR status in accordance with various embodiments;

FIG. 7 is an exemplary table of alternative RS risk groups with PR status in accordance with various embodiments;

FIGS. 8A and 8B represent an exemplary table of the mean, standard deviation, and range of primary QTA parameters at SSF=0.4 to SSF=1 (and no filter) in accordance with various embodiments;

Figure 9B:
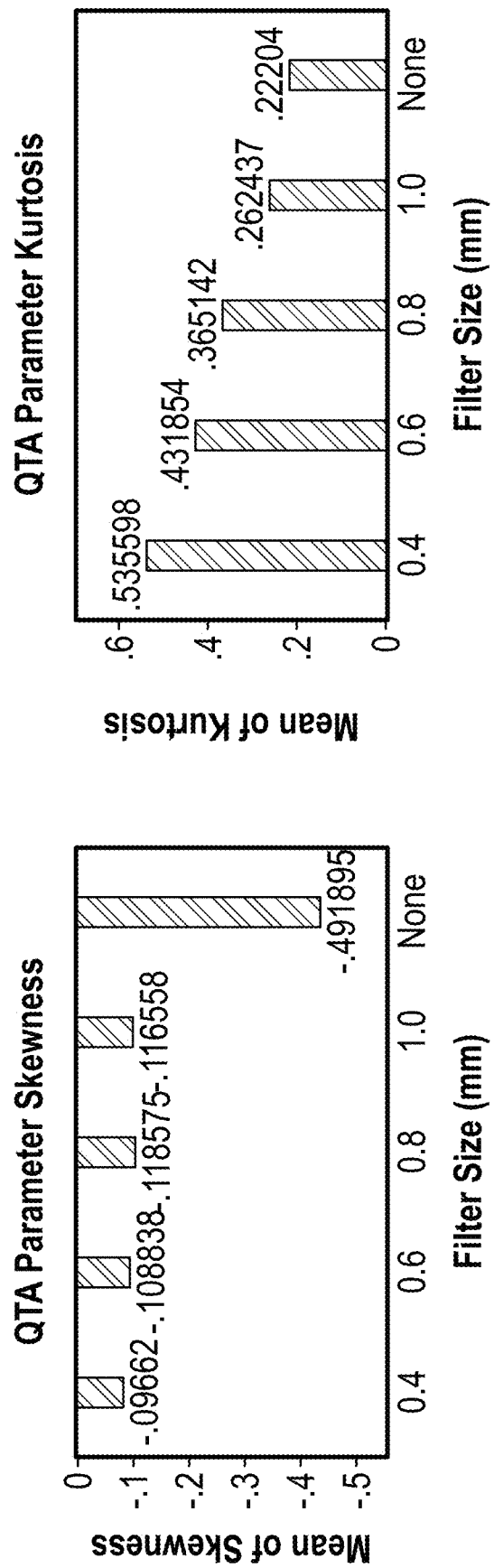
Figure 11:
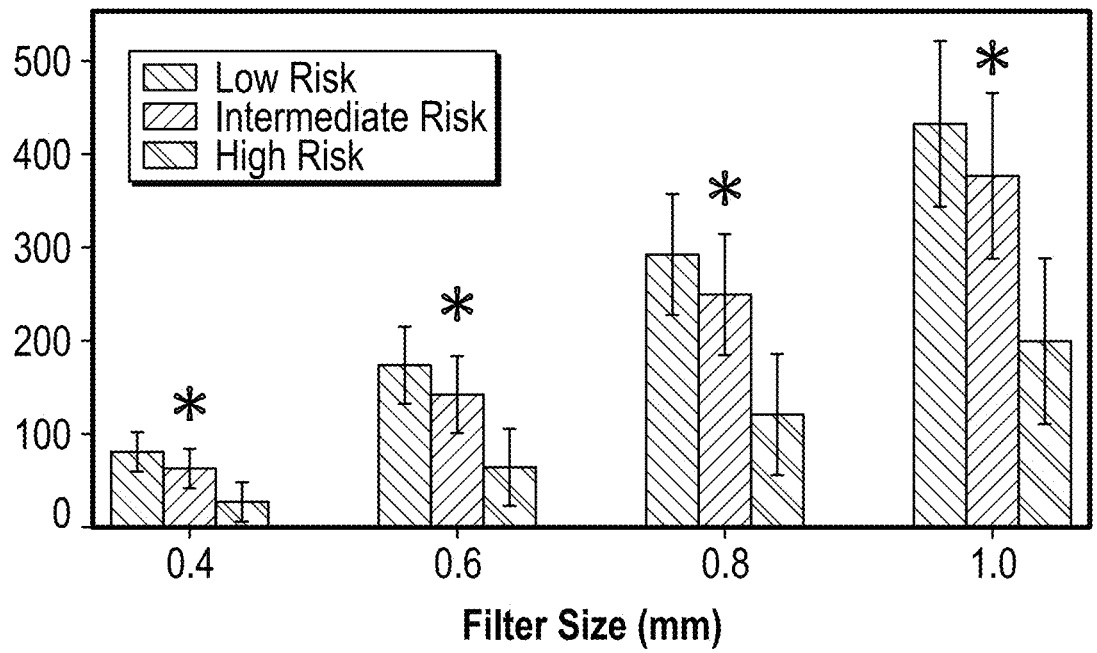
Figure 12:
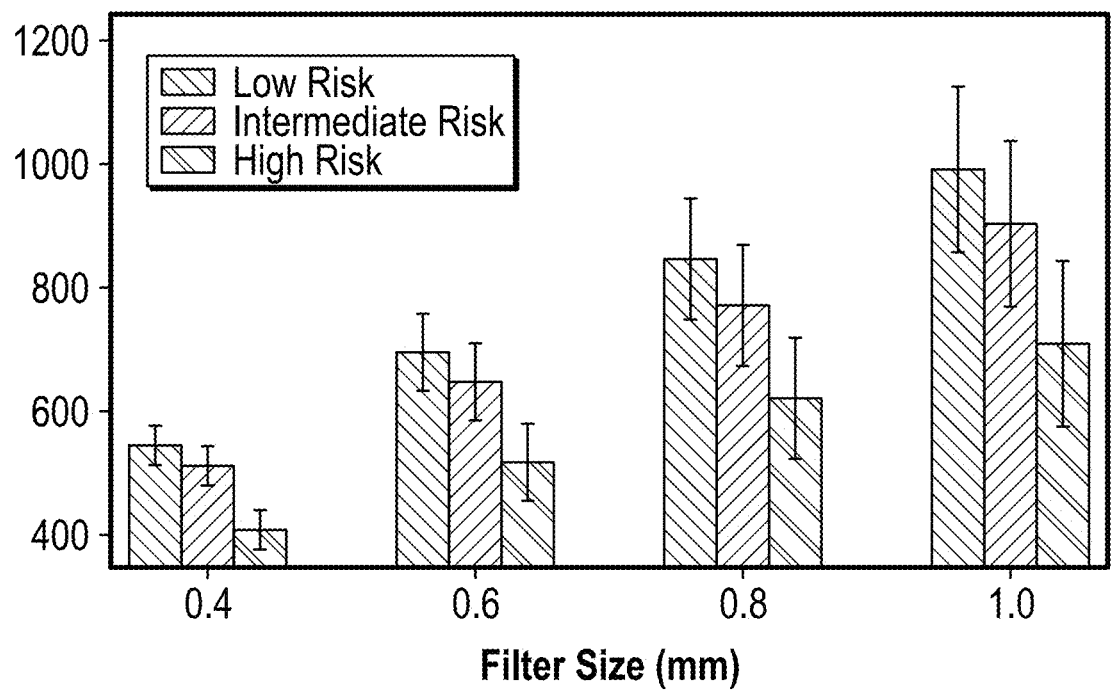
Figure 13:
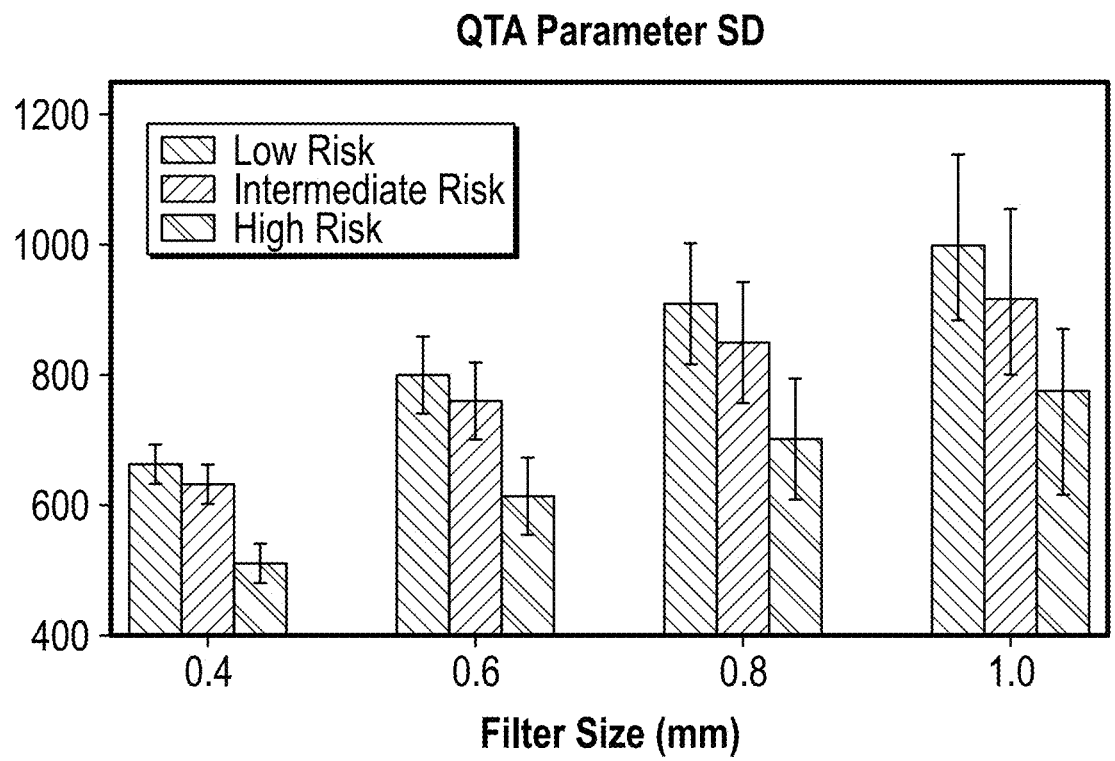
Figure 14:
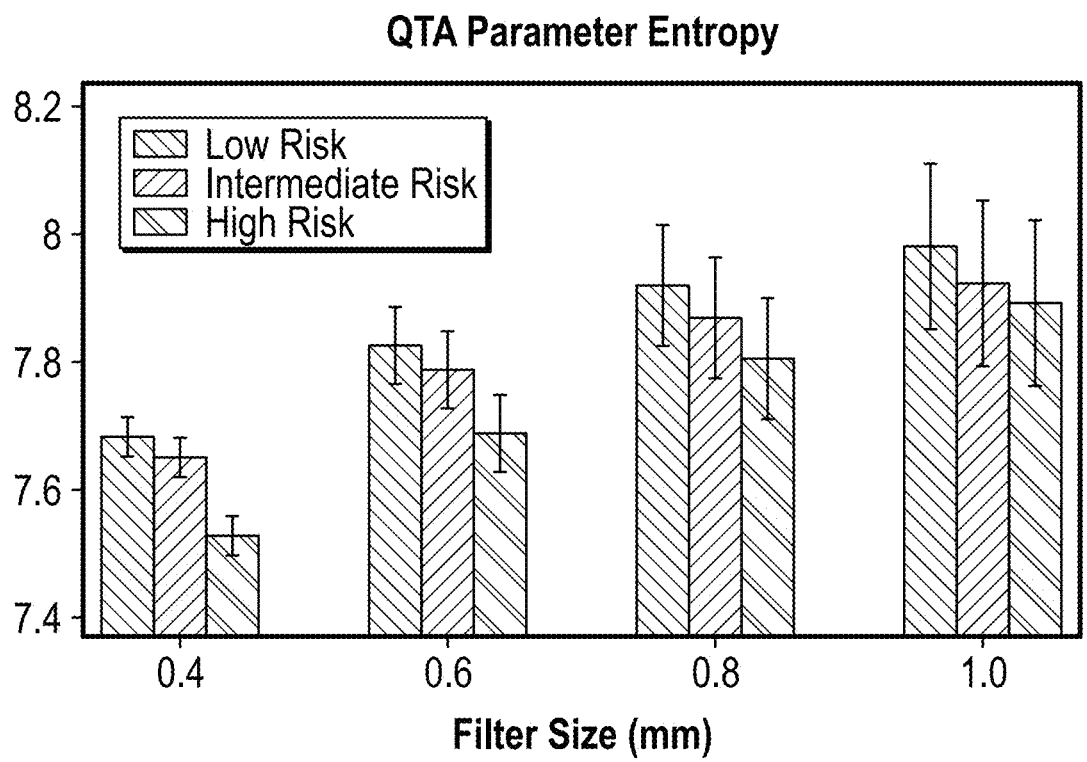
Figure 15:
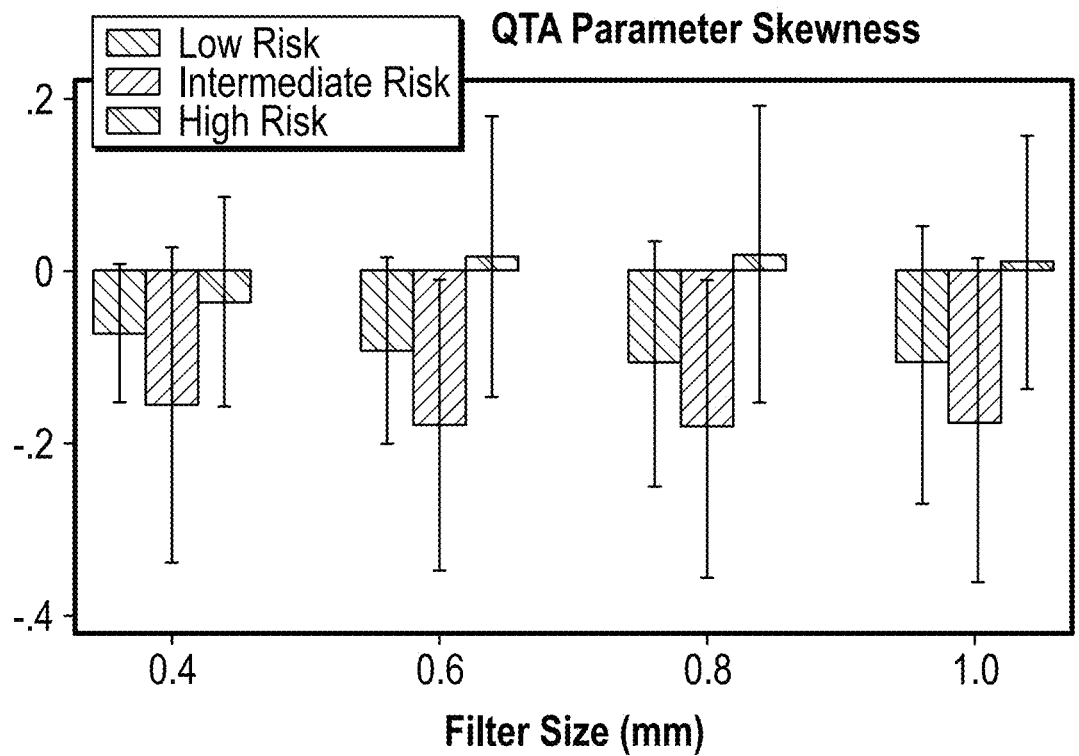
Figure 16:
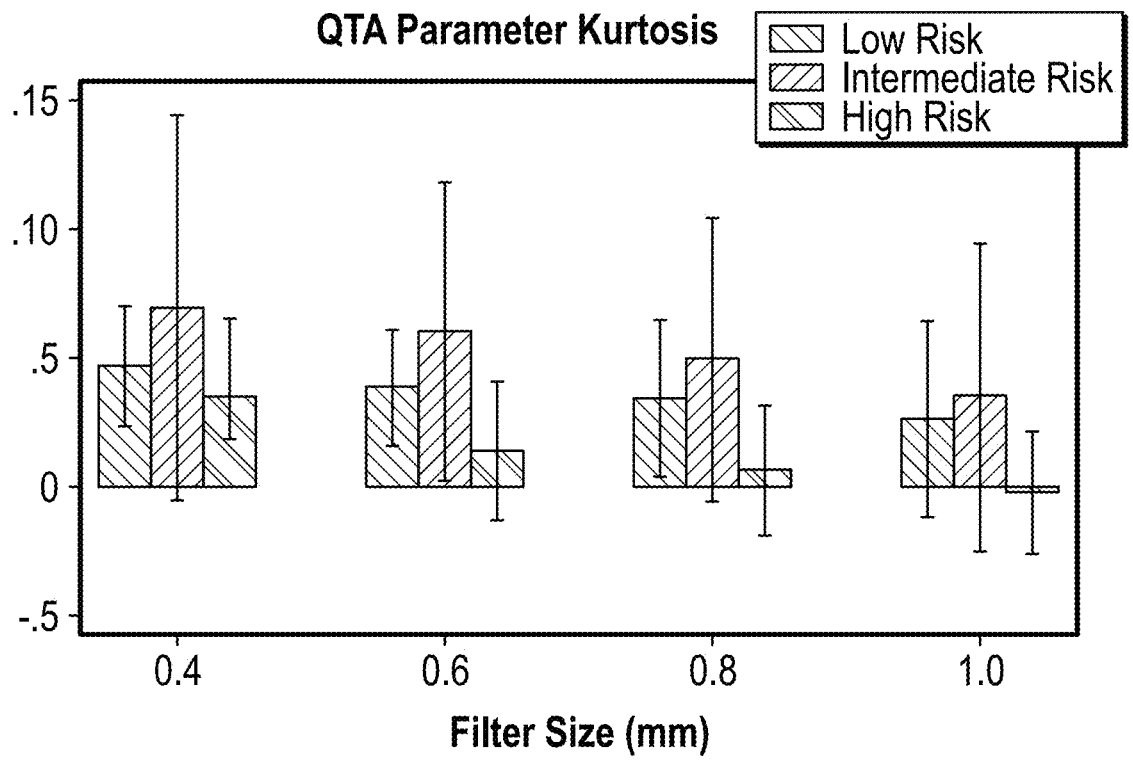
Figure 17:
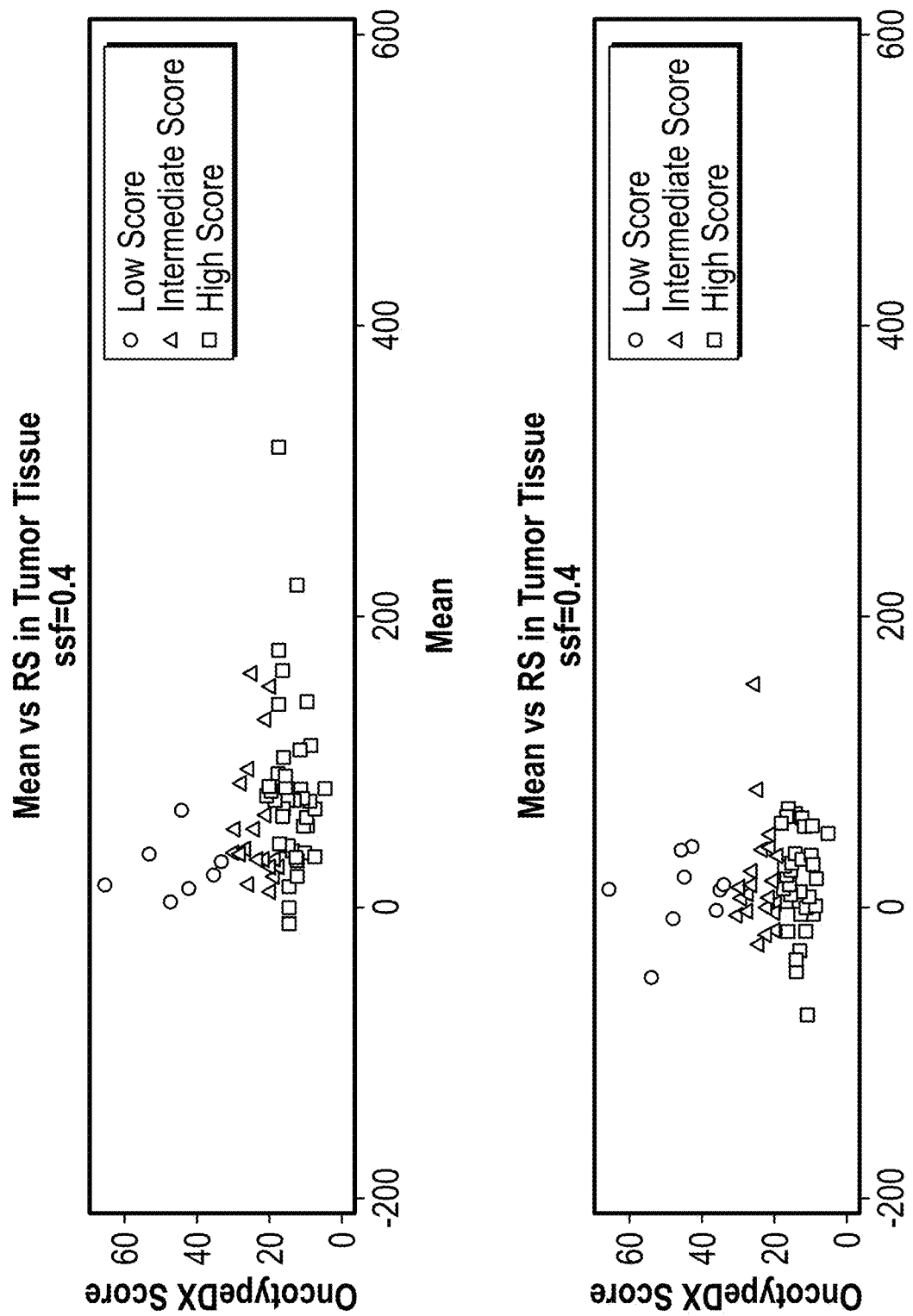

FIGS. 9A and 9B graphically depict exemplary mean values of primary QTA parameters at SSF=0.4 mm to 1 mm in accordance with various embodiments;

FIGS. 10A and 10B represent an exemplary table of t Test comparisons in accordance with various embodiments;

FIGS. 11-16 graphically depict exemplary mean and standard deviation values for primary QTA parameters for low, intermediate, and high RS risk groups in accordance with various embodiments;

FIG. 17 graphically depicts raw data of RS versus the QTA parameter Mean for exemplary tumor and normal tissue in accordance with various embodiments;

FIG. 18 is an exemplary table of best fit QTA based linear model for predicting log (RS) in accordance with various embodiments; and FIG. 19 is an exemplary table of best fit QTA based logistic model for predicting high risk RS in accordance with various embodiments.

DETAILED DESCRIPTION OF PREFERRED EXEMPLARY EMBODIMENTS

The following detailed description of the invention is merely exemplary in nature, and neither the scope of the invention nor the application and uses of the invention are limited to the embodiments set forth herein.

The present invention uses QTA to derive a series of signatures useful in determining whether breast cancer is sufficiently aggressive such that it is likely return after hormone treatment. In this regard, mammographic imaging data, analytical techniques such as QTA, and logistical regression algorithms are powerful tools; yet they are only tools. By themselves, they do not advance cures. Rather, the ingenuity, creativity, commitment, and passion—in short, the inspiration and perspiration of human researchers—must ultimately be brought to bear on these technologies. The foregoing analytical tools are employed by the cancer researcher just as the chisel and rasp are used by the sculptor to coax a work of art out of a slab of marble. The present inventor has successfully employed QTA and logistical regression techniques on aggregate imaging data for unambiguously known hi RS tumors and unambiguously known low RS tumors to develop a statistically reliable signature for predicting tumor aggressiveness in new breast cancer images.

Various embodiments include the steps of: i) obtaining mammography image data for a first population of high RS breast tumors and a second population of low RS breast tumors; ii) selecting a region of interest (ROI) surrounding the tumor in the form of a rectangle, Ellipse, polygon, seed point, or other region encompassing the tumor and loading the image data onto a suitable QTA platform (e.g., TexRAD); iii) selecting an appropriate filter algorithm (e.g., Mammo general, Mammo fine); iv) filtering the pixels to a single common size and shape and clustering them together as nearest neighbors into groups of 2, 3, 4, 5, and 6 pixels and applying different spatial scale filters (SSFs); v) generating a histograph frequency curve for each SSF; vi) deconstructing each curve to yield parameters (metrics) including, for example, mean pixel density, standard deviation of the histogram curve, mean positive pixel value of the pixels that are in the positive value range, entropy, skewness, and kurtosis; vii) displaying the metric values in a matrix or otherwise representing the values in the form of equations; viii) performing logistical regression on the matrix values; and ix) using the results of the logistical regression individually or in combination with other clinical, laboratory, imaging, demographic, or other bio-informatics to create signatures useful in predicting tumor aggressiveness.

Figure 1:
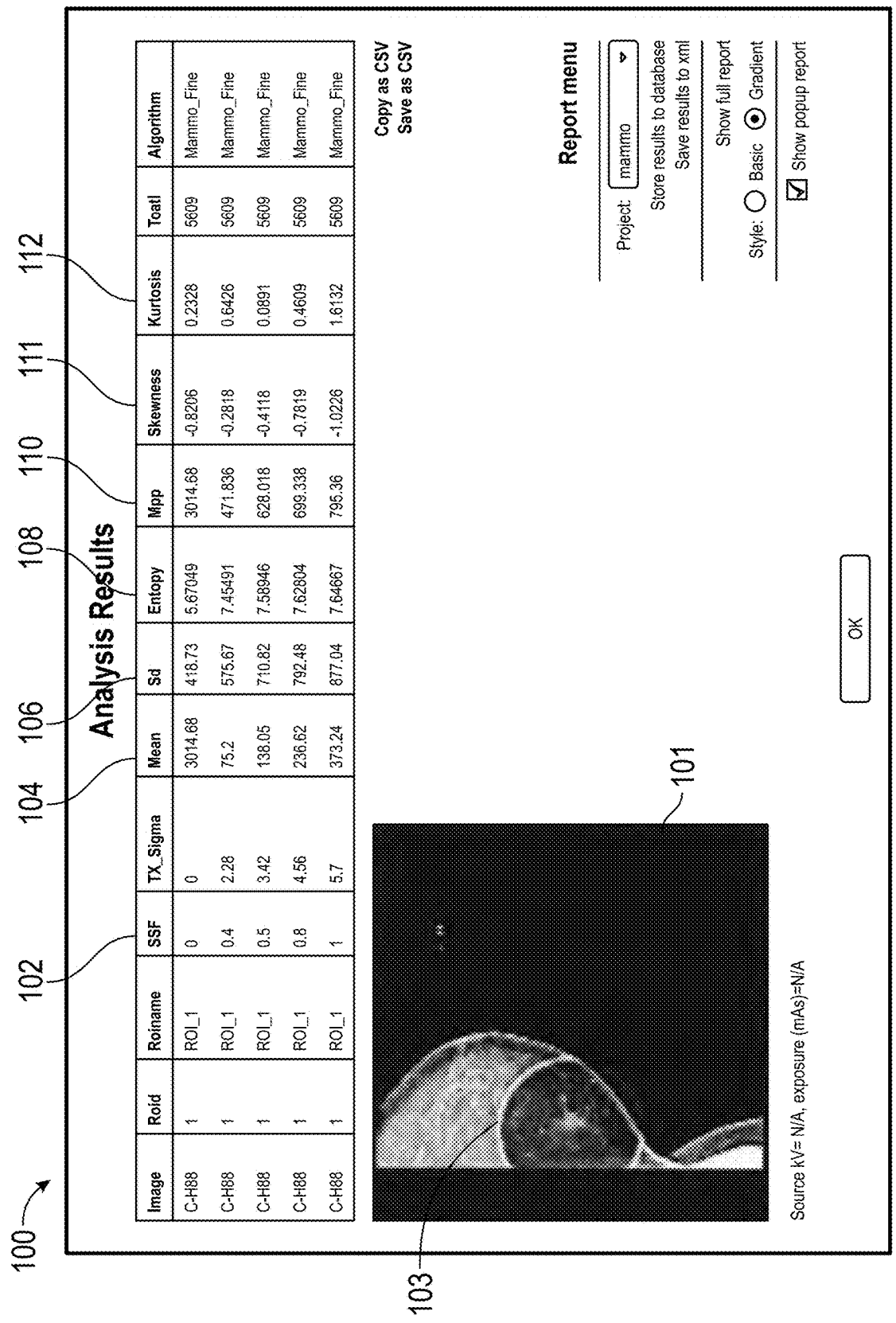
FIG. 1 is an exemplary breast tumor image and associated image parameters (metrics), illustrating a region of interest (ROI) in accordance with various embodiments.

QTA was performed using the TexRAD platform developed at the University of London, Sussex, on archived digital mammograms for which subsequent pathology reports were available. Referring now to FIG. 1, for each of a plurality of DICOMM compatible radiology images 101, tumor lesions were visually identified by drawing regions of interest (ROI) 103 around the target lesions. A single button click then performed detailed measurement and transformation of the gray level intensity of each pixel in the ROI, followed by image filtration (Laplacian of Gaussian) using 5 filter levels 102 (sizes 0.4 mm, 0.6 mm, 0.8 mm, 1 mm, and no filter), to yield various image metrics including the mean 104, standard deviation 106, entropy 108, mean positive pixel value 110, skewness 112, and kurtosis 114.

Figure 2:
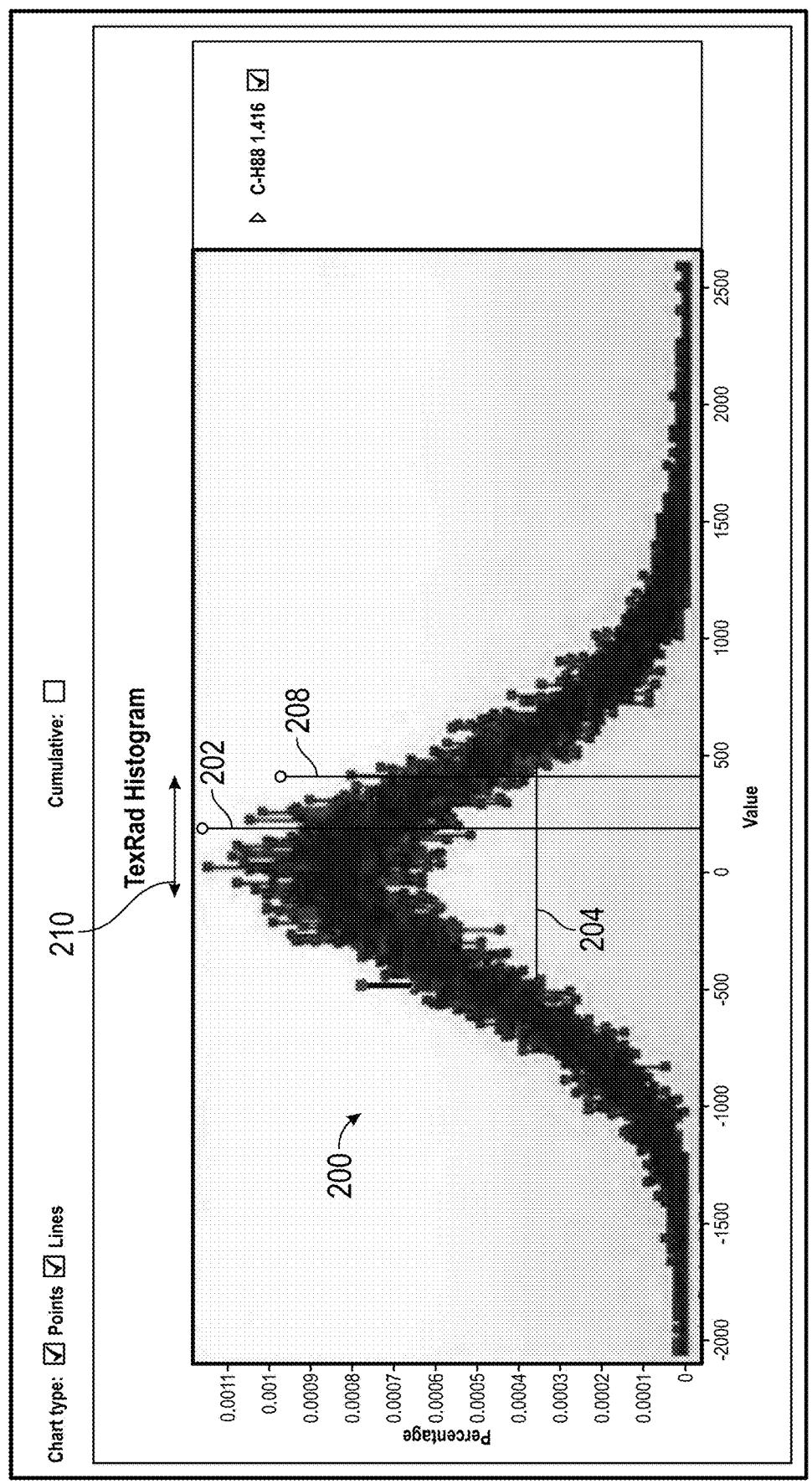
FIG. 2 is an exemplary histogram curve in accordance with various embodiments.

Referring now to FIG. 2, a histogram 200 of filtered pixel intensity vs. number of pixels is shown for the data in FIG. 1. The filter, also known as SSF, is used to cluster small groups of pixels together in order to measure local density changes. The histogram 200 illustrates the following QTA parameters:

Mean 202—Measures the average density within a cluster of pixels at a given SSF level, measured in Hounsfield unit (HU). HU measurements between 0-20 indicates fluid, 20-80 soft tissue, >80 calcium or metal, <0 to −100 fat, and <−100 air. The mean is sometimes regarded as a measure of necrosis.

Standard deviation (SD) 204—Measures the spread of density distribution in the filtered image. The natural logarithm of mean pixel density normalized to the total number of pixels. It is a measure of heterogeneity and microstructural changes in the entire ROI.

Entropy—Measures the mean density of clustered pixels within the ROI, i.e. irregularity in the ROI. A measure of heterogeneity.

Mean positive pixel values (MPP) 208—Measures the average density of positive pixel values. A measure of hypoxia.

Skewness 210—Measures the sharpness of density distribution. Positive skewness (i.e. slant of the peak to the left) may reflect angiogenesis.

Kurtosis—Measures the symmetry of density distribution. A measure of angiogenesis, vascular shunting, and tumor homogeneity.

Next, a ROI of nearly identical size was drawn in the normal tissue of the same mammogram and QTA parameters in the same five SSF levels were obtained from the ROI of the normal tissue. Similar QTA processing was done for microcalcification tissue in mammograms where microcalcification lesions were visually identifiable.

The measured QTA parameters were outputted from TexRAD as a .csv file and imported to a verified Excel spreadsheet for derivation of additional QTA parameters. Referring now to FIG. 3, the following three additional sets of QTA parameters were derived for each filter level based on the primary QTA parameters 302:

1) QTA parameters 304 normalized to the size of ROI by dividing the values of primary QTA parameters (Mean, SD, Entropy, MPP, Skewness, and Kurtosis) by the total number of pixels in the ROI for each filter level. The normalized parameters are referred to herein as Mean-Total, SD-Total, Entropy-Total, MPP-Total, Skewness-Total, and Kurtosis-Total.

2) The maximal change or range 306 in each primary parameter across the SSF levels, referred to herein as Mean-Range, SD-Range, Entropy-Range, MPP-Range, Skewness-Range, Kurtosis-Range. Note that these values are the same for all SSF levels of a given tissue type (tumor or normal tissues) in the same subject.

3) The difference 308 between the primary QTA parameters of the tumor and normal tissues, referred to herein as Mean-Diff, SD-Diff, Entropy-Diff, MPP-Diff, Entropy-Diff, Skewness-Diff, and Kurtosis-Diff. Note that these values are the same for tumor and normal tissues at the same SSF level in the same subject.

The foregoing derivations may be performed automatically, for example, by Excel functions and Stata programs; alternatively, they may be done manually.

The foregoing histogram and the associated metrics embody biological information, which the present inventor seeks to harness and express as models useful in predicting breast tumor aggressiveness. Specifically, the present inventor seeks to characterize the data in terms of one or more signatures against which future patient scans may be evaluated to predict breast tumor aggressiveness with a high degree of confidence.

More particularly, each patient's Oncotype DX® Recurrence Score (RS) was used to assess tumor aggressiveness. This score is the result of the 21-Gene Oncotype DX Breast Cancer Assay, a genomic assay clinically validated and recommended by major guidelines for all node-negative, ER+ breast cancer patients. The score directly correlates with the 10-year distant recurrence rate, with an RS score >30 considered high risk, score between 18 and 30 inclusive considered intermediate risk, and score <18 considered low risk. A more recent, alternative risk criterion considers RS score >25 as high risk and score <11 as low risk. RS was collected from Oncotype pathology reports. In addition, ER and PR status, if available, were also collected from the biopsy or surgery pathology reports.

Statistical analysis was carried out using STATA/IC version 13 on a PC.

With reference to FIG. 4, it is known that many biological variables do not meet the underlying assumptions of parametric statistical tests (e.g. linear regression). For example, biological data often are not normally distributed, nor the variances of the residuals homogeneous; in other words, they do not exhibit normality or homoscedasicity. Standard data transformation, such as log or square-root transformation, preserves the monotonicity of the data, while simultaneously improving the normality and the homoscedasicity of the variables; the effect is often clear especially when there is a large number of observations. Therefore, in order to examine such data using parametric statistical analysis, it is often helpful to transform the data from primary QTA parameters 402 to transformed QTA parameters 404. In an embodiment, log (base-10) and square-root transformation were both utilized to improve normality and homoscedasicity of the data as a predicate to linear regression analysis. Untransformed data was used in the logistic regression analysis, because logistic regression does not assume normal and homoscedastic data.

QTA parameters are evaluated to assess whether they can predict RS by performing robust multiple linear regression using RS as the dependent variable (or outcome), and using QTA parameters and age as independent variables (or predictors). A linear model is considered statistically significant if the t-statistics of every predictor in the model is >2 (i.e. greater than 2 standard deviations) and its associated p-value is <=0.05. The fitness of the linear model is determined by examining F-statistics and the associated p-value: The best-fit linear model has the highest F-statistics and the lowest associated p-value. Conventional algorithms for linear regression may be used to control heteroskedasticity, an assumption of linear regression that implies that the variance of the residuals should be constant.

For each SSF level, the best-fit linear regression model of RS was found using backward step-wise elimination, which consisted of two steps: First, Spearman rank correlation was performed between RS and each of QTA parameters with significance level of 0.20, allowing for the identification of any QTA parameters that may combine to have significance contribution in the final model. Next, linear regression was performed iteratively, dropping the predictor with the biggest p-value greater than 0.05 each time, until all predictors have p-value less or equal to 0.05. This analysis was done three times, first time including PR status as a predictor, second time without PR status, and third time examining PR+ patients only. The rationale for the first two analyses was that PR status may not be known at the time of QTA.

The third analysis allowed us to see if QTA parameters can predict RS in PR+ population. All best-fit linear models were found with a custom program written in Stata 13 programming language that implemented the backward step-wise elimination algorithm as outlined; the automation minimized manual errors and allowed for reproduction of models.

The resulting linear models were examined with regression diagnostic tools, including check for normalized residuals via STATA's distributional diagnostic plots (e.g. kdensity, pnorm, qnorm) and the Shapiro-Wilk Test, check for severe outliers with the Interquartile Range Test, check for collinearity via Variance Inflation Factors and condition index tests, check for homoscedasticity via graph of residuals vs. predicted values, check for model specification via specification link test, and check for omitted variables via the Ramsey (1969) regression specification-error test (RESET).

Second, QTA parameters were assessed to determine whether they can predict high risk RS (both RS>30 and RS>25) by performing multiple logistic regression using high RS as the outcome (1 if RS>30 or 25, 0 otherwise), and QTA parameters and age as predictors, also employing backward step-wise elimination. This analysis was done three times, first time including PR status as a predictor, second time without PR status, and third time examining PR+ patients only. The rationales for the three times logistic regression analysis is the same as those for linear regression analysis.

Following each logistic regression analysis, the log likelihood $chi^2$ value of the model was checked to see if the model as a whole was statistically significant. Hosmer and Lemeshow's goodness of fit test was employed to examine the fit of the logistic models; that is, how well the model is able to predict the outcome. A link test was also performed to detect model specification error, which could mean either that log it function (used in logistic regression) was not the correct function to use, or that the relationship between the log it of the outcome and the predictors was not linear. Collinearity of the predictors was also checked using STATA's collinearity test. Finally, ROC analysis was performed on the best-fit model to assess the discrimination of the model, which is how well the model distinguishes patients who have high risk RS from those have non-high risk RS. The ROC area under curve (AUC) was recorded.

In one embodiment, 142 patients were identified based on the eligibility requirement, but 78 were eliminated because of one or more of the following reasons: Had microcalcification lesion only, no tumor lesion that was visually identifiable on the mammograms, no verifiable Oncotype DX® Recurrence Score (RS), or had multiple tumor lesions with different hormonal status and/or RS. After exclusion, 64 patients remained. One of the patients had 2 tumor lesions with identical hormonal status and RS and, therefore, statistical analysis was performed on 65 data points. For each patient, QTA was performed on a single tumor lesion at SSF levels 0.4, 0.6, 0.8, 1, and 0 (SSF=0 means no filter).

The mean age at the time of diagnosis was 61 (standard deviation=11 years) and ranged from 36 to 83. The patients' ER and PR status are shown in FIG. 5.

The RS had a mean of 20 (standard deviation=11) and ranged from 4 to 65. As mentioned previously, the standard thresholds for risk stratification are RS<18 for low risk, 18<=RS<=30 for intermediate risk, RS>30 for high risk. However, recent studies have attempted to elucidate the tumor aggressiveness of patients in the intermediate risk RS group (18<=RS<=30) by stratifying risk group with a different set of thresholds: RS<11 for low risk, 11<=RS<=25 for intermediate risk, and RS>25 for high risk. FIGS. 6 and 7 show the breakdown of the 64 patients into the three risk groups, based on the two definitions. FIGS. 8A and 8B list the mean, standard deviation, and range of the primary QTA parameters in tumor tissues at SSF levels 0.4, 0.6, 0.8, 1, and 0. FIGS. 9A and 9B show the average values of the QTA parameters as the filter (SSF) changes from 0.4 mm to 1.0 mm and also when there is no filter.

It was observed that at each SSF level, the average values of QTA parameters differed among the three RS risk groups, demonstrated in FIGS. 10-16. Among the QTA parameters, Mean showed the most statistically significant difference between the high and non-high risk groups (i.e. low and intermediate risk groups). Highest t statistic was observed at SSF=0.8, where QTA parameter Mean of the tumor tissue was lower in the high risk RS group than in the low or intermediate risk RS group (Intermediate vs. high risk group: $t=3.1756$, $p=0.0044$. Low vs. high risk group: $t=4.2251$, $p=0.0002$), see FIGS. 10 and 11. This relationship between RS and Mean was observed at all SSF levels except for SSF=0 (no filter). Furthermore, this relationship was not observed in normal tissue, as shown in FIG. 17.

Referring now to FIG. 18, QTA parameters were isolated that showed correlation with RS risk group using Spearman rank correlation test, and then tested for linear relationship between QTA parameters and RS. The following show the results from the linear modeling.

If PR status was unknown and therefore not included, the best-fit linear model had SD as the predictor at SSF=0.4 ($n=65$, $F=6.89$, $p=0.0108$, $R2=0.0870$). Statistically significant linear models were also found at SSF=0.6 and 0.8. The value of PR in the linear models was either zero for PR− or one for PR+.

If PR status was known and included, the best-fit linear model had PR and Skewness-Diff as statistically significant predictors at SSF=1 ($n=65$, $F=15.30$, $p<0.0001$, $R2=0.2988$). Statistically significant linear model was also found at SSF=0.4 ($n=65$, $F=10.74$, $p<0.0001$, $R2=0.3224$).

Among PR+ patients, linear regression showed that QTA parameter Skewness-Diff is a statistically significant predictor of log(RS) at SSF=0.8 and 1 (At SSF=0.8, $n=58$, $F=9.36$, $p=0.0034$, $R2=0.1320$. At SSF=1, $n=58$, $F=7.25$, $p=0.0093$, $R2=0.0770$.). No statistically significant models for predicting RS among PR+ patients were found at SSF=0.4, 0.6, and 0.

All three linear models showed no severe outliers and exhibited normalized residuals; they also succeeded model specification test and omitted variables test. However, their condition numbers exceeded 10 and less than 30, which indicated that the linear models were slightly unstable but not severely so.

FIG. 19 depicts the logistic relationship between QTA parameters and RS risk group. The following summarizes the results from the logistic modeling.

Statistically significant logistic models were identified with QTA parameters as explanatory variables in predicting the probability of being in the standard high risk group (RS>30) or in the alternative high risk group (RS>25).

Among PR+ patients, QTA parameter, SD-Diff, was shown to be a statistically significant predictor for the probability of having high risk RS with RS>30 ($n=58$, $chi^2=6.87$, $p=0.0087$, $AUC=0.9212$, $SE=0.0515$). Also among PR+ patients, QTA parameters, Skewness and SD-Diff, were shown to be statistically significant predictors for the probability of the patient being in the alternative high risk group with RS>25 ($n=58$, $chi2=9.68$, $p=0.0079$, $AUC=0.8814$, $SE=0.0453$).

In the "Logistic Model" column of FIG. 19, note thet exp denotes exponential, and $$\log it(Pr) = \ln Pr/(1-Pr)$$

where Pr is the probability or likelihood of having high risk RS (RS>30 or RS>25), and $Pr/(1-Pr)$ is the odds of having high risk RS given the QTA parameters.

Note that when there is a single quantitative explanatory variable for predicting high risk RS, the log it function can be solved directly for Pr in that case.

All logistic models for predicting high risk RS succeeded the link test, Hosmer and Lemeshow's goodness of fit test, and the collinearity check.

The foregoing analysis suggests that QTA can be used to reliably characterize breast tumor aggressiveness. Specifically, various embodiments reveal a correlation between RS risk group and QTA parameters, specifically membership in high risk group and QTA Mean. QTA parameter Mean was lower in high risk RS group than non-high risk RS group with statistical significance at all SSF levels except when SSF=0 (see FIGS. 10 and 11). Since QTA Mean is a measure of necrosis, it means that high risk RS correlates with higher necrosis. As a control, it was observed that there was no such difference in the Means between high risk RS and non-high risk RS groups in normal tissues (see FIG. 17). Non-parametric analysis confirmed that multiple QTA parameters correlated with RS.

Next, models (also referred to as signatures or biomarker signatures) were derived for predicting RS or RS risk group using QTA parameters as predictors. PR status was found to be a significant predictor in addition to the QTA parameters. Introduction of PR status as a predictor allowed for better fit linear and logistic regression models. In fact, there was a statistically significant difference in the mean RS between PR+ and PR− patients in one sample of 64 patients ($t=3.5146$, $p=0.0113$): 7 PR-patients had a mean RS of 38 and 57 PR+ patients had a mean RS of 17. This 21-point difference explains why including PR status increased the goodness of fit in both linear and logistic models.

To understand the predictive power of QTA, the best-fit models were identified when PR status was included as a predictor, when PR status was not included as a predictor, and when subjects were PR+ patients only. Best-fit linear models were derived that can predict RS (see FIG. 18) as well as best-fit logistic models that can predict RS high risk group (see FIG. 19), all with p-value <0.02. Below are the findings:

When PR status is unknown, QTA parameter SD can be used to predict RS ($b=-0.0004177$, $t=-2.63$, $p=0.011$) in a linear model at SSF=0.4. This inverse relationship between SD and RS may appear contradictory at first, as one would expect tumor heterogeneity to increase with tumor aggressiveness. However, recall that SD represents the distribution of the density distribution, and that the Means of high risk RS group were highly clustered on the low end of Mean spectrum, unlike the wide-spread distribution of the Means of the low and intermediate risk RS groups (see FIG. 17). Hence SD is expected to be lower for high risk RS (i.e. more aggressive tumor).

When PR status known, PR status ($b=-0.3759396$, $t=-5.28$, $p=0.000$) and QTA parameter Skewness-Diff ($b=0.0785932$, $t=2.63$, $p=0.011$) can be used together to predict RS in a linear model at SSF=1. Recall that Skewness measures the symmetry of density distribution, and hence as the symmetry difference between tumor and normal tissue increases (i.e. a positive skewness delta), RS would increase based on the model. This is in accordance with the previous report that positive Skewness may reflect angiogenesis.

Analysis also showed that Skewness-Diff may be used alone in a linear model at SSF=0.8 to predict RS among PR+ patients.

QTA parameter Entropy Diff can be used to predict the probability of having RS>30. The ROC AUC for this model is 0.8424 (SE=0.0717), indicating that model is able to discriminate moderately well. The present inventor proposes a cut point of Entropy Diff=0.021 (sensitivity=85.71%, specificity=67.24%, LR+=2.6165, LR−=0.2125); that is, Entropy Diff less than 0.021 in tumor tissue indicates a high probability of RS>30.

QTA parameter Mean-Total can be used to predict the probability of having RS>25. The ROC AUC is 0.7437 (SE=0.0612), indicating that the discrimination of the model is only fair. A cut point of Mean-Total=0.00769932 is proposed (sensitivity=75.00%, specificity=64.15%, LR+=2.0921, LR−=0.3897); a Mean-Total less than 0.00769932 in tumor tissue indicates a high probability of RS>25.

When PR status is known, PR status and SD-Diff can be used together to predict the probability of having RS>30. The ROC AUC is 0.9409 (SE=0.0322), which means the model can distinguish patients with RS>30 well. PR status and Mean-Total can also be used together to predict the probability of having RS>25. The ROC AUC is 0.8443 (SE=0.0591), which means the model can distinguish patients with RS>25 moderately well.

The foregoing analysis reveals a plurality of relationships, which may expressed in the form of equations, which are useful in predicting high risk RS scores. By way of non-limiting illustration and referring again to FIG. 18, where PR status is not included, linear modeling suggests that SD is a predictor and an exemplary signature may be expressed as $\log(RS) = -0.0004177*(SD) + 1.500248$ for SSF=0.4. If PR status is included (PR=0 for PR−, and PR=1 for PR+), linear modeling suggests that PR and [Skewness-Diff] are predictors and an exemplary signature may be expressed as $\log(RS) = -0.3759396*(PR) +$ $0.0785932*(\text{Skewness-Diff}) + 1.592273$ for SSF=1. For PR+ patients, linear modeling suggests that [Skewness-Diff] is a predictor and an exemplary signature may be expressed as $\log(RS) = 0.3033226*(\text{Skewness-Diff}) + 2.83791$ for SSF=0.8.

By way of further illustration and referring again to FIG. 19, where PR status is not included, logistic modeling suggests that [Entropy-Diff] is a predictor and an exemplary signature may be expressed as $p = e^x/[1+e^x]$ for SSF=0; where $x = -5.905371*(\text{Entropy-Diff}) - 2.2254296$,

SSF=0, and high risk RS is defined as RS>30. For RS>25 and PR status is not included, logistic modeling suggests that [Mean-Total] is a predictor and an exemplary signature may be expressed as $p = e^x/[1+e^x]$; where $x = -140.810e[\text{Mean-Total}] - 0.2993403$ for SSF=0.6.

If PR status is included (PR=0 for PR−, and PR=1 for PR+), logistic modeling suggests that PR and [SD-Diff] are predictors and an exemplary signature may be expressed as $\log it(p) = -3.548941*(PR) - 0.0092257*[\text{SD-Diff}]$ $+0.363196$ for SSF=0 and RS>30;

where $\log it(Pr) = \ln(Pr/[1-Pr])$,

Pr is the probability or likelihood of having high risk RS (e.g., RS>30 or RS>25), and (Pr/[1−Pr]) is the odds of having high risk RS given the QTA parameters. Note that where there is a single quantitative explanatory variable for predicting high risk RS, the log it function can be solved directly for Pr in that case.

With continued reference to FIG. 19, for RS>25 and PR status included, logistic modeling suggests that PR and [Mean-Total] are predictors and an exemplary signature may be expressed as $\log it(p) = -4.321735*(PR) - 159.0879*[\text{Mean-Total}]$ $+3.430188$ for SSF=0.6.

For PR+ patients, logistic modeling suggests that [SD-Diff] is a predictor and an exemplary signature may be expressed as $p = e^x/[1+e^x]$; where $x = -0.0124166*[\text{SD-Diff}] - 3.547383$ for SSF=0, and RS>30.

For PR+ patients and RS>25, logistic modeling suggests that [MPP-Diff] and [Skewness-Diff] are predictors and an exemplary signature may be expressed as $\log it(p) = -0.0095748*[\text{MPP-Diff}]$ $+6.487719*[\text{Skewness-Diff}] - 2.2761748;$ For SSF=0.6

The present inventor thus posits that tumor heterogeneity in digital mammograms, as quantified by QTA analysis, shows promising opportunity in predicting breast cancer tumor aggressiveness, as measured by Oncotype DX® Recurrence Score (RS). Given the statistically significant results in linear prediction of RS and in logistic prediction of high risk RS, it is believed that QTA offers great potential in quantifying tumor aggressiveness in a non-invasive, real-time, cost-effective way. QTA analysis and its relationship to tumor biology provides a clinically relevant application of QTA in breast cancer risk stratification and corresponding prediction of treatment response.

A biomarker signature is thus provided for use in identifying breast tumors having a high risk Oncotype DX Assay Recurrence Score (RS), which breast tumors are to analyzed subsequent to deriving the signature. The signature is derived through linear modeling of a first population of prior images having low risk RS scores, and a second population of prior images having high risk RS scores. The signature may be expressed in the form of the equation log (RS)=Mx+B, where M is a coefficient, x is a QTA-based parameter, and B is a constant.

In an embodiment, the signature is derived using a spatial scale filter (SSF) value of 0.4, and x corresponds to Standard Deviation (SD).

In an embodiment, M has a value in the range of −0.0001 to −0.001, and B has a value in the range of 1 to 2; in particular M is about −0.0004177, and B is about 1.500248.

In an embodiment, the signature is further derived using progesterone receptor (PR) status where PR−=0 and PR+=1. The signature may be expressed in the form log (RS)=N (PR)+Mx+B, where N is a coefficient.

In an embodiment, the signature is derived using a spatial scale filter (SSF) value of 1, and x corresponds to the QTA-based parameter [Skewness-Diff].

In an embodiment, N is in the range of −0.1 to −1; M is in the range of 0.01 to 0.1, and B is in the range of 1 to 2. In particular, N is about −0.3759396; M is about 0.0785932; and B is about 1.592273.

In an embodiment, the first and second populations have only PR+ status, the signature is derived using a spatial scale filter (SSF) value of 0.8, and x corresponds to [Skewness-Diff].

In an embodiment, M has a value in the range of 0.1 to 1, and B has a value in the range of 1 to 4; in particular, M is about 0.3033226; and B is about 2.83791.

A signature is also provided for use in identifying breast tumors having a probability p of exhibiting a high risk RS score. The signature is derived from high risk and low risk legacy tumor data using logistic modeling, and expressed in the form p=ex/[1+ex], where x=Ay+B, and: A is a coefficient; Y is a QTA based parameter; and B is a constant.

In an embodiment, the PR status of the legacy tumor data is not considered; Y corresponds to the QTA parameter [Entropy-Diff]; the logistic model employed an SSF value of 0; and high risk RS>30.

In an embodiment, A is about −6, and B is about −2.

In an embodiment, the PR status of the legacy tumor data is not considered; Y corresponds to the QTA parameter [Mean-Total]; the logistic model employed an SSF value of 0.6; and high risk RS>25.

In an embodiment, A is about −140, and B is about −0.3.

In an embodiment, the legacy tumor data have only PR+ status; the signature is derived using a spatial scale filter (SSF) value of 0; high risk RS>25; and Y corresponds to [SD-Diff].

In an embodiment, A is about −0.01, and B is about −0.3.

A signature is also provided for use in identifying breast tumors having a probability log it(p) of exhibiting a high risk RS score. The signature is derived from high risk and low risk legacy tumor data using logistic modeling and expressed in the form log it(p)=C(PR)+Ay+B, where: PR−=0 and PR+=1; C is a first coefficient; A is a second coefficient; y is a QTA-based parameter; and B is a constant.

In an embodiment, RS>30; SSF=0; C is about 3; A is about −0.01; y is [SD-Diff] and B is about 0.4.

In an embodiment, RS>30; SSF=0; C is about 3; A is about −0.01; y is [SD-Diff]; and B is about 0.4.

As used herein, the word "exemplary" means "serving as an example, instance, or illustration." Any implementation described herein as "exemplary" is not necessarily to be construed as preferred or advantageous over other implementations, nor is it intended to be construed as a model that must be literally duplicated.

While the foregoing detailed description will provide those skilled in the art with a convenient road map for implementing various embodiments of the invention, it should be appreciated that the particular embodiments described above are only examples, and are not intended to limit the scope, applicability, or configuration of the invention in any way. To the contrary, various changes may be made in the function and arrangement of elements described without departing from the scope of the invention.

The invention claimed is:

1. A method of predicting responsiveness of breast tumors to hormone therapy, the method comprising:
    performing a quantitative textual analysis (QTA) based on a breast scan for a patient;
    determining using the QTA based on the breast scan for the patient, a particular value for a QTA-based parameter;
    estimating an Oncotype DX Assay Recurrence Score (RS) value for the patient using a biomarker signature for use in identifying subsequent breast tumors having a high risk Oncotype DX Assay RS, and the particular value for the QTA based parameter,
        wherein the biomarker signature was derived through linear modeling of a first population of prior images having low risk RS scores and a second population of prior images having high risk RS scores, the biomarker signature expressed in the form $$\log(RS)=Mx+B, \text{ where:}$$

M is a coefficient;
    x is the QTA-based parameter; and
    B is a constant; and
    predicting responsiveness to hormone therapy for the patient based on the estimated RS value.

2. The method of claim 1, wherein the biomarker signature is derived using a spatial scale filter (SSF) value of 0.4, and x corresponds to a standard deviation (SD).

3. The method of claim 2, wherein:
    M has a value in the range of −0.0001 to −0.001; and
    B has a value in the range of 1 to 2.

4. The method of claim 3, wherein:
    M is about −0.0004177; and
    B is about 1.500248.

5. The method of claim 1, wherein the biomarker signature is further derived using progesterone receptor (PR) status where PR−=0 and PR+=1, and the biomarker signature expressed in the form $$\log(RS)=N(PR)+Mx+B$$

where N is a coefficient.

6. The method of claim 5, wherein the biomarker signature is derived using a spatial scale filter (SSF) value of 1, and x corresponds to the QTA-based parameter [Skewness-Diff].

7. The method of claim 6, wherein:
    N is in the range of −0.1 to −1;
    M is in the range of 0.01 to 0.1; and
    B is in the range of 1 to 2.

8. The method of claim 7, wherein:
    N is about −0.3759396;
    M is about 0.0785932; and
    B is about 1.592273.

9. The method of claim 1, wherein:
    the first and second populations have only PR+ status;
    the signature is derived using a spatial scale filter (SSF) value of 0.8; and
    x corresponds to [Skewness-Diff].

10. The method of claim 9, wherein:
M has a value in the range of 0.1 to 1; and
B has a value in the range of 1 to 4.

11. The method of claim 9, wherein:
M is about 0.3033226; and
B is about 2.83791.

12. A method of predicting responsiveness of breast tumors to hormone therapy, the method comprising:
performing a quantitative textual analysis (QTA) based on a breast scan for a patient;
determining using the QTA based on the breast scan for the patient, a particular value for a QTA-based parameter;
estimating a recurrence score (RS) value for the patient using a biomarker signature for use in identifying breast tumors having a probability p of exhibiting a high risk RS value, the signature derived from high risk and low risk legacy tumor data using logistic modeling and expressed in the form $p = ex/[1+ex]$ where $x = Ay + B$, and:

A is a coefficient;
Y is a QTA based parameter; and
B is a constant; and
predicting responsiveness to hormone therapy for the patient based on the estimated RS value.

13. The method of claim 12, wherein:
the PR status of the legacy tumor data is not considered;
Y corresponds to the QTA parameter [Entropy-Diff];
the logistic model employed an SSF value of 0; and
high risk RS>30.

14. The method of claim 13, wherein:
A is about −6; and
B is about −2.

15. The method of claim 12, wherein:
a PR status of the legacy tumor data is not considered;
Y corresponds to a QTA parameter [Mean-Total];
the logistic model employed an SSF value of 0.6; and
high risk RS>25.

16. The method of claim 15, wherein:
A is about −140; and
B is about −0.3.

17. The method of claim 12, wherein:
the legacy tumor data have only PR+ status;
the biomarker signature is derived using a spatial scale filter (SSF) value of 0;
a high risk RS>25; and
Y corresponds to [SD-Diff].

18. The method of claim 17, wherein:
A is about −0.01; and
B is about −0.3.

19. A method of predicting responsiveness of breast tumors to hormone therapy, the method comprising:
performing a quantitative textual analysis (QTA) based on a breast scan for a patient;
determining using the QTA based on the breast scan for the patient, a particular value for a QTA-based parameter;
estimating a recurrence score (RS) value for the patient using a biomarker signature for use in identifying breast tumors having a probability log it(p) of exhibiting a high risk RS value, the signature derived from high risk and low risk legacy tumor data using logistic modeling and expressed in the faun $\log it(p) = C(PR) + Ay + B$ where:

PR−=0 and PR+=1;
C is a first coefficient;
A is a second coefficient;
y is a QTA-based parameter; and
B is a constant; and
predicting responsiveness to hormone therapy for the patient based on the estimated RS value.

20. The method of claim 19, wherein:
RS>30; SSF=0;
C is about 3;
A is about −0.01;
y is [SD-Diff]; and
B is about 0.4.

21. The method of claim 19, wherein:
RS>30; SSF=0;
C is about 3;
A is about −0.01;
y is [SD-Diff]; and
B is about 0.4.

* * * * *